United States Patent
Pekander et al.

(10) Patent No.: US 9,918,637 B2
(45) Date of Patent: *Mar. 20, 2018

(54) SYSTEM AND METHOD FOR MONITORING PATIENT PHYSIOLOGICAL DATA

(71) Applicant: GENERAL ELECTRIC COMPANY, Schenectady, NY (US)

(72) Inventors: Otto Valtteri Pekander, Espoo (FI); Kristian Matti Karru, Kirkkonummi (FI)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/135,819

(22) Filed: Apr. 22, 2016

(65) Prior Publication Data

US 2016/0310047 A1    Oct. 27, 2016

(30) Foreign Application Priority Data

Apr. 24, 2015 (GB) .................................. 1507058.4

(51) Int. Cl.
*A61B 5/00* (2006.01)
*A61B 5/117* (2016.01)
(Continued)

(52) U.S. Cl.
CPC ............ *A61B 5/002* (2013.01); *A61B 5/0059* (2013.01); *A61B 5/117* (2013.01); *A61B 5/6803* (2013.01);
(Continued)

(58) Field of Classification Search
CPC .......... H04Q 9/00; H04Q 9/14; A61B 5/0002; G08C 17/02; A61N 1/37211
See application file for complete search history.

(56) References Cited

U.S. PATENT DOCUMENTS 8,475,367 B1    7/2013  Yuen et al.
2009/0076840 A1 3/2009  Boyden et al.
(Continued)

FOREIGN PATENT DOCUMENTS

WO    2009120147 A2    10/2009
WO    2013096954 A1    6/2013

OTHER PUBLICATIONS

Combined Search and Exam Report for corresponding GB Appln. No. 1507058.4, dated Oct. 27, 2015, 6 pages.
(Continued)

*Primary Examiner* — Ted Wang
(74) *Attorney, Agent, or Firm* — Andrus Intellectual Property Law, LLP

(57) ABSTRACT

A system for monitoring patient physiological data is disclosed herein. The system comprises a wireless patient monitoring device with a known device identity having a first sensor for retrieving patient physiological data, and a data reception device comprising a processor for processing data received via a wireless communication protocol from the patient monitoring device and a memory for storing the known patient monitoring device identity, the memory being connected to an identity input device for entering the known patient monitoring device identity. The data reception device can receive and process identification data to obtain a patient monitoring device identity and to compare said identity with the stored known identity. When the identity matches, the data reception device is allowed to receive and process the retrieved patient physiological data. The patient monitoring device comprises a visual identification and the identity input device comprises an optical sensor for retrieving the visual identification.

12 Claims, 4 Drawing Sheets

(51) Int. Cl.
   *G06F 19/00*   (2018.01)
   *A61B 5/1172*  (2016.01)
(52) U.S. Cl.
   CPC ............ *G06F 19/30* (2013.01); *A61B 5/1172* (2013.01); *A61B 5/742* (2013.01); *A61B 2562/08* (2013.01)

(56) References Cited

U.S. PATENT DOCUMENTS

| | | | |
|---|---|---|---|
| 2010/0076337 A1* | 3/2010 | Medina | A41D 13/1281 600/549 |
| 2013/0130622 A1 | 5/2013 | Yang et al. | |
| 2013/0317753 A1 | 11/2013 | Kamen et al. | |
| 2014/0013100 A1 | 1/2014 | Menzel et al. | |
| 2014/0067426 A1 | 3/2014 | Neff | |
| 2014/0275872 A1* | 9/2014 | Merritt | A61B 5/14551 600/322 |
| 2015/0141772 A1 | 5/2015 | LeBoeuf et al. | |
| 2016/0183836 A1* | 6/2016 | Muuranto | A61B 5/04288 600/301 |

OTHER PUBLICATIONS

Combined Search Report and Exam Report for corresponding GB Application No. 1507057.6, dated Oct. 28, 2015, 7 pages.

\* cited by examiner

SYSTEM AND METHOD FOR MONITORING PATIENT PHYSIOLOGICAL DATA

The present disclosure relates to a system and a method for monitoring patient physiological data, wherein the system comprises a wireless patient monitoring device adapted to retrieve patient physiological data and able to communicate with a data reception device comprising a processor for processing the retrieved patient physiological data. The data reception device typically comprises a patient monitor with a screen for visualizing patient physiological data.

BACKGROUND

In an environment for treatment of patients, such as a hospital, the use of wireless patient monitoring devices is known. Such a wireless patient monitoring device typically comprises a sensor which is connected to the body of a patient and is adapted to retrieve patient physiological data. The wireless patient monitoring device comprises an emitter for sending the retrieved patient physiological data to a data reception device which typically comprises a bedside patient monitor. The patient monitor is adapted to receive the patient physiological data and comprises a screen which allows visual access to patient physiological data.

Additionally or alternatively, the wireless patient monitoring device is connected, using a wireless communication protocol, to a hospital network.

Prior to allowing the wireless patient monitoring device to send data to the bedside patient monitor and/or the hospital network, the wireless patient monitoring device must be paired to the receiving device of the bedside monitor and/or the hospital network and must be associated with the right patient. In a hospital environment, patient association, which means guaranteeing the right association between retrieved patient physiological data and a known patient, is one of the greatest concerns relating to the use of wireless patient monitoring. If patient association is not correctly performed, the wireless patient monitoring device will produce patient data and associate such data with the wrong patient.

According to the prior art, patient association comprises pairing between a wireless patient monitoring device and a data reception device, such as a bedside monitor, by entering a known patient monitoring device identity in the data reception device. Such known patient monitoring device identity is entered into a memory of the data reception device prior to use of the wireless patient monitoring device. The wireless patient monitoring device is adapted to send both retrieved patient physiological data and sensor identification data. Accordingly, the data reception device receives and processes sensor identification data with the aim of comparing the received sensor identification data with the stored known patient monitoring device identity. Such comparison allows the data reception device to verify whether the patient physiological data received is being sent by the appropriate wireless patient monitoring device.

The ability of the data reception device to compare stored known patient monitoring device identity with received sensor identification data constitutes a safety measure which guards against receiving patient physiological data from an unknown or non-identified wireless patient monitoring device.

The data reception device also comprises a memory for storing known patient identities. After confirmation that the data reception device is communicating with the right wireless patient monitoring device, the data reception device processes the received patient physiological data and combines this with the correct known patient identity stored in a memory of the data reception device.

A data reception device according to the prior art is provided with an input device for entering the identity of a wireless patient monitoring device.

A first manner of entering the identity of a wireless patient monitoring device is the use of a keyboard, wherein an operator is required to manually type in the known identity of a wireless patient monitoring device. A disadvantage of the use of such known input devices is the risk of operator-related errors. For example, an operator could easily mistype the identity of a wireless patient monitoring device, with no control system available to automatically correct such errors.

A second manner of entering the identity of a wireless patient monitoring device into the memory of a data reception device is the use of specific identifiers or tags, such as barcodes. The information on identifiers can be read with specific readers, such as barcode readers. A disadvantage of the use of such specific readers is that they are relatively expensive and voluminous. Data reception devices, such as bedside monitors, are generally becoming smaller, with reduced size increasing the user-friendliness and mobility of data reception devices. The size of known readers, such as barcode readers, tends to be disproportionately large compared to the size of data reception devices.

In the prior art, Radio Frequency Identification (RFID) techniques are used to allow pairing between wireless patient monitoring devices and data reception devices. A disadvantage of RFID techniques, such as Near Field Communication (NFC) technology, is that they are relatively expensive. Enabling wireless patient monitoring devices with known RFID techniques means that they become relatively expensive to produce and thus precludes the use of wireless patient monitoring devices as disposables.

In practice, a patient to whom a wireless patient monitoring device is attached may be moved from a first environment, wherein the wireless patient monitoring device communicates with a first data reception device, to a second location wherein the wireless patient monitoring device communicates with a further data reception device. This can occur, for example, when a patient is moved from a first hospital room to a second hospital room. Where a wireless patient monitoring device is to send retrieved patient physiological data to a new data reception device, the wireless patient monitoring device and the data reception device must once again follow a procedure to allow pairing of the two devices in order to safeguard correct data transmission and reception between the devices. It will be evident that each time a new connection between a wireless patient monitoring device and a data reception device needs to be established, the procedures and techniques that allow pairing according to the prior art are relatively time-consuming and open to operator error.

It is possible to link the retrieved patient physiological data to a patient identity, in which case the patient identity can be used to retrieve a patient file available in a hospital network and to link the retrieved patient physiological data directly to the appropriate patient file. Where physiological data is to be directly linked to a patient file, patient identity should be entered in the wireless patient monitoring device.

In view of the identified disadvantages of the known systems and devices, there is an apparent need for a safe and inexpensive input device for entering an identity of a wireless patient monitoring device.

SUMMARY OF THE INVENTION

The present disclosure is directed to a system and a method for monitoring patient physiological data. This can be achieved by the features as defined by the independent claims. Further enhancements are characterized in the dependent claims.

In one aspect, the present disclosure is directed to a system for monitoring patient physiological data, comprising:

a wireless patient monitoring device with a first sensor adapted for retrieving patient physiological data, the wireless patient monitoring device having a known patient monitoring device identity, a data reception device comprising a processor for processing data received from the wireless patient monitoring device and a memory for storing the known patient monitoring device identity, the memory being connected to an identity input device for entering the known patient monitoring device identity, said wireless patient monitoring device being adapted to send retrieved patient physiological data and identification data to said data reception device using a wireless communication protocol, said data reception device being adapted to receive and process identification data to obtain a patient monitoring device identity and to compare said identity with stored known patient monitoring device identity to allow the data reception device, in case of a matching identity, to receive and process the retrieved patient physiological data, wherein the wireless patient monitoring device comprises a visual identification and wherein the identity input device comprises an optical sensor for retrieving said visual identification.

In a further aspect, the present disclosure is directed to a method for monitoring patient physiological data with a wireless patient monitoring device with a first sensor adapted to retrieve patient physiological data and a data reception device for receiving and processing said patient physiological data, the data reception device being connected to a memory, the wireless patient monitoring device having a known identity associated with identification data, wherein the wireless patient monitoring device and the data reception device are adapted to communicate using a wireless communication protocol, the method comprising:

storing the known wireless patient monitoring device identity in the memory connected to the data reception device, using the wireless patient monitoring device to send the identification data to the data reception device using a wireless communication protocol, using the data reception device to receive and process the identification data to retrieve the identity of the wireless patient monitoring device, comparing the retrieved identity of the wireless patient monitoring device with the stored known wireless patient monitoring device identity, if the retrieved identity of the wireless patient monitoring device matches the stored known wireless patient monitoring device identity, pairing the wireless patient monitoring device with the data reception device to allow the wireless patient monitoring device to retrieve and send patient physiological data to the data reception device and to allow the data reception device to receive and process said retrieved patient physiological data, the method further comprising:

providing the wireless patient monitoring device with a visual identification relating to its identity, providing the data reception device with an optical sensor for obtaining an image of the visual identification of the wireless patient monitoring device, wherein storing the known wireless patient monitoring device identity in the memory connected to the data reception device comprises obtaining an image of the visual identification of the wireless patient monitoring device using the optical sensor of the data reception device and processing the image to retrieve the wireless patient monitoring device identity.

At least one of the above embodiments provides one or more solutions to the problems and disadvantages of the background art. Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Figure 1:
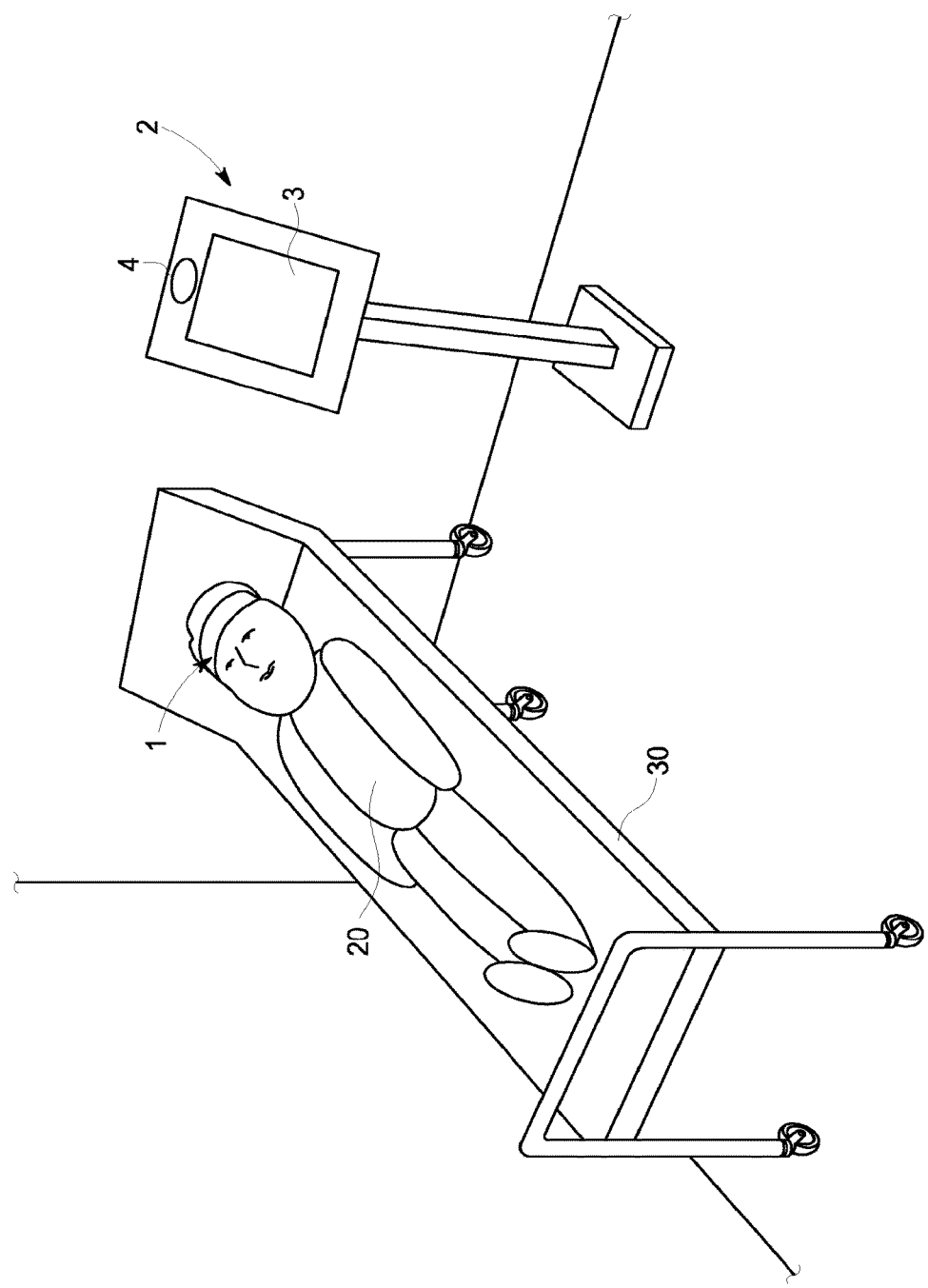
FIG. 1 is a diagrammatic illustration of a system for monitoring patient physiological data according to an exemplary embodiment of the disclosure.

FIG. 1 shows an exemplary embodiment of a system for monitoring patient physiological data comprising a wireless patient monitoring device 1 which is attached to a patient 20, wherein the patient is positioned on a bed 30. The wireless patient monitoring device 1 is shown in more detail in FIG. 2.

The wireless patient monitoring device 1 comprises a first sensor which is adapted to retrieve patient physiological data. In order to be able to retrieve such patient physiological data, the wireless patient monitoring device comprises electronic components which allow for retrieval of the patient physiological data. In addition to electronic components for retrieving patient physiological data, the wireless patient monitoring device 1 also comprises an electronic circuit which allows the wireless patient monitoring device 1 to emit and forward data to a data reception device 2 which is adapted to receive and process such data. The electronic components are schematically indicated with reference number 12.

In the example of FIG. 1, the data reception device 2 comprises a bedside monitor. The bedside monitor is provided with a screen 3 which is used to display the patient physiological data to allow visual access to said data.

The wireless patient monitoring device 1 is provided with an identity for wireless patient monitoring device 1. The identity is typically a unique identity or UID. The electric circuit of the wireless patient monitoring device 1 is adapted to not only emit and forward retrieved patient physiological data, but also sensor identification data relating to the identity of wireless patient monitoring device 1.

In a first embodiment of the wireless patient monitoring device 1, the number of components which the wireless patient monitoring device 1 comprises is limited, for the purposes of making the wireless patient monitoring device 1 as small, simple and inexpensive as possible. If the wireless patient monitoring device 1 comprises only an electronic circuit adapted to retrieve and forward retrieved physiological data in combination with the identification data, the wireless patient monitoring device 1 could be used as a disposable. Thus, after a single use of the wireless patient monitoring device 1 with a first patient 20, the wireless patient monitoring device 1 may be destroyed. The possibility of using the wireless patient monitoring device 1 as a disposable allows for enhanced user-friendliness of the wireless patient monitoring device 1. This is particularly advantageous for the control of contagious diseases, as it would not be necessary to recover and prepare the wireless patient monitoring device 1 for further use with another patient.

The data reception device 2 is adapted to receive the identification data emitted by the wireless patient monitoring device 1. The data reception device 2 comprises, or is connected to, a processor which is able to process the received identification data in order to retrieve the identity of the wireless patient monitoring device 1 which has emitted said identification data. The data reception device 2 also comprises a memory for storing a known patient monitoring device identity of a wireless patient monitoring device 1 with which the data reception device 2 is to communicate.

In practice, the use of the wireless patient monitoring device 1 in combination with the data reception device 2 is as follows: prior to allowing communication between the wireless patient monitoring device 1 and the data reception device 2, the identity for the wireless patient monitoring device 1 is entered into the memory of the data reception device 2 as a known patient monitoring device identity. The entry of this known patient monitoring device identity allows the data reception device 2 to compare the identification data received from any wireless patient monitoring device with said known wireless monitoring device identity for the purposes of verifying whether the data reception device 2 is receiving data from the right wireless patient monitoring device.

After the entry of known patient monitoring device identity in the memory of the data reception device 2, the wireless patient monitoring device 1 commences emitting identification data and retrieved patient physiological data. The known patient monitoring device identity is entered using an identity input device. In a first step, the data reception device 2 receives the identification data emitted by the wireless patient monitoring device 1 and processes such data in order to obtain the identity of the wireless patient monitoring device from which the identification data was generated. In a further step, the data reception device 2 compares the obtained wireless patient monitoring device identity with the known patient monitoring device identity, which is stored in the memory of the data reception device 2. If the data reception device 2 is able to match the obtained wireless patient monitoring device identity with the known patient monitoring device identity, the data reception device 2 allows pairing between the emitting wireless patient monitoring device 1 and the data reception device 2. Thereafter, the data reception device 2 is able to receive the patient physiological data retrieved using the wireless patient monitoring device 1 and is able to process said patient physiological data. After processing the patient physiological data, the data reception device 2 is adapted to display the patient physiological data on the screen 3 of the data reception device 2.

Figure 2:
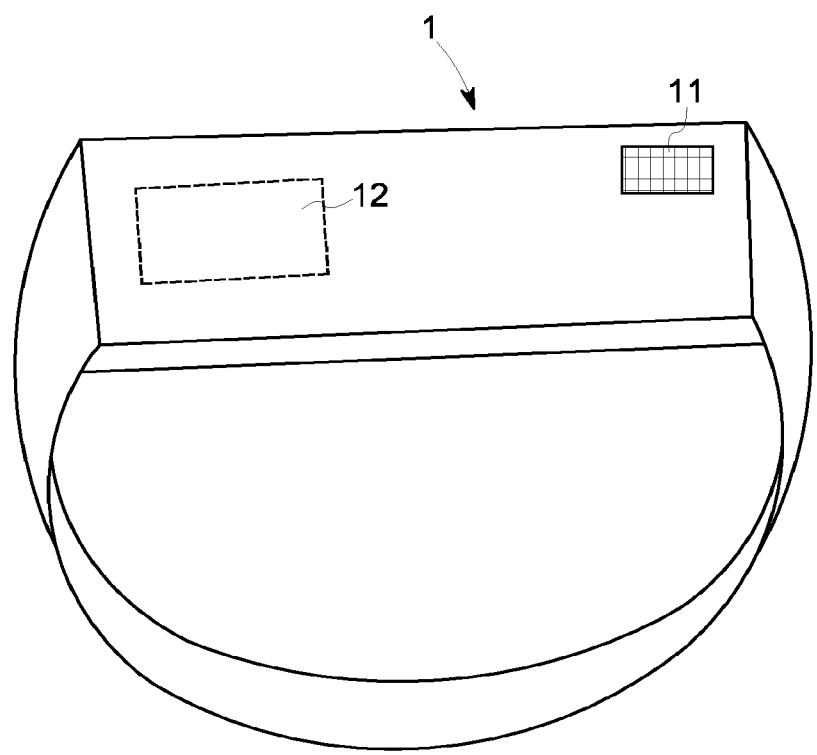
FIG. 2 is a diagrammatic illustration of a wireless patient monitoring device used in the system for monitoring patient physiological data according to an exemplary embodiment of the disclosure.

According to the present disclosure, the data reception device 2 comprises an identity input device 4 in the form of an optical sensor. The identity input device 4 is, for instance, a camera. To allow entry of an identity using a camera, the wireless patient monitoring device 1 comprises a physical identification 11. This is shown in FIG. 2. The identity input device 4 is adapted to obtain the visual identification 11 and to process the visual identification 11 to retrieve the known patient monitoring device identity for the wireless patient monitoring device 1. The identity input device 4 is connected to the memory of the data reception device 2 to allow the known patient monitoring device identity to be stored in the memory of the data reception device.

It will be understood that the wireless patient monitoring device 1 in combination with the data reception device 2 according to the present disclosure allows for a safe and user-friendly procedure for entering known patient monitoring device identity into the memory of the data reception device 2. Prior to the use of the wireless patient monitoring device 1, the wireless patient monitoring device 1 is positioned in front of the identity input device 4 to allow the identity input device 4 to obtain an image of the visual identification 11 on the exterior of the wireless patient monitoring device 1. Thereafter, with no need for operator intervention, the unique and correct identity of the wireless patient monitoring device 1 is entered into the memory of the data reception device 2 as the known patient monitoring device identity. The use of both the visual identification 11 displayed on the wireless patient monitoring device 1 and the identity input device 4 allows for a procedure with no risk of entering a wrong or invalid identity as the known wireless patient monitoring device identity.

In FIG. 2, an exemplary embodiment of a wireless patient monitoring device 1 is shown with a visual identification 11 which is visible from the exterior of the wireless patient monitoring device 1. The visual identification 11 can be any suitable visual identification of which an image can be taken with an optical sensor to retrieve, after processing with an adapted image recognition technique, a unique identity of the wireless patient monitoring device 1. As an example, the visual identification 11 could comprise QR code.

In the example of FIGS. 1 and 2, the data reception device 2 is connected to a further input device (not shown) which is used for entering and storing a known patient identity. The known patient identity comprises information relating to the patient 20 whose physiological data is to be retrieved. The known patient data can comprise the name of the patient and, for instance, information relating to social security, health insurance and other patient-related data which is commonly used in hospital procedures. In a hospital network, each patient has a patient file in which all patient-related information is recorded. Identification of the patient is required to link the retrieved patient physiological data to the right patient file. The input device for entering the known patient identity can comprise a keyboard for entering information in the data reception device 2, or, where the data reception device 2 is in the form of a tablet, an active part of the screen 3 adapted to enter information in the data reception device 2.

In practice, the data reception device 2 is adapted to link the known patient identity with the retrieved patient physiological data once the correct pairing between the wireless patient monitoring device 1 and the data reception device 2 has been established.

Figure 3:
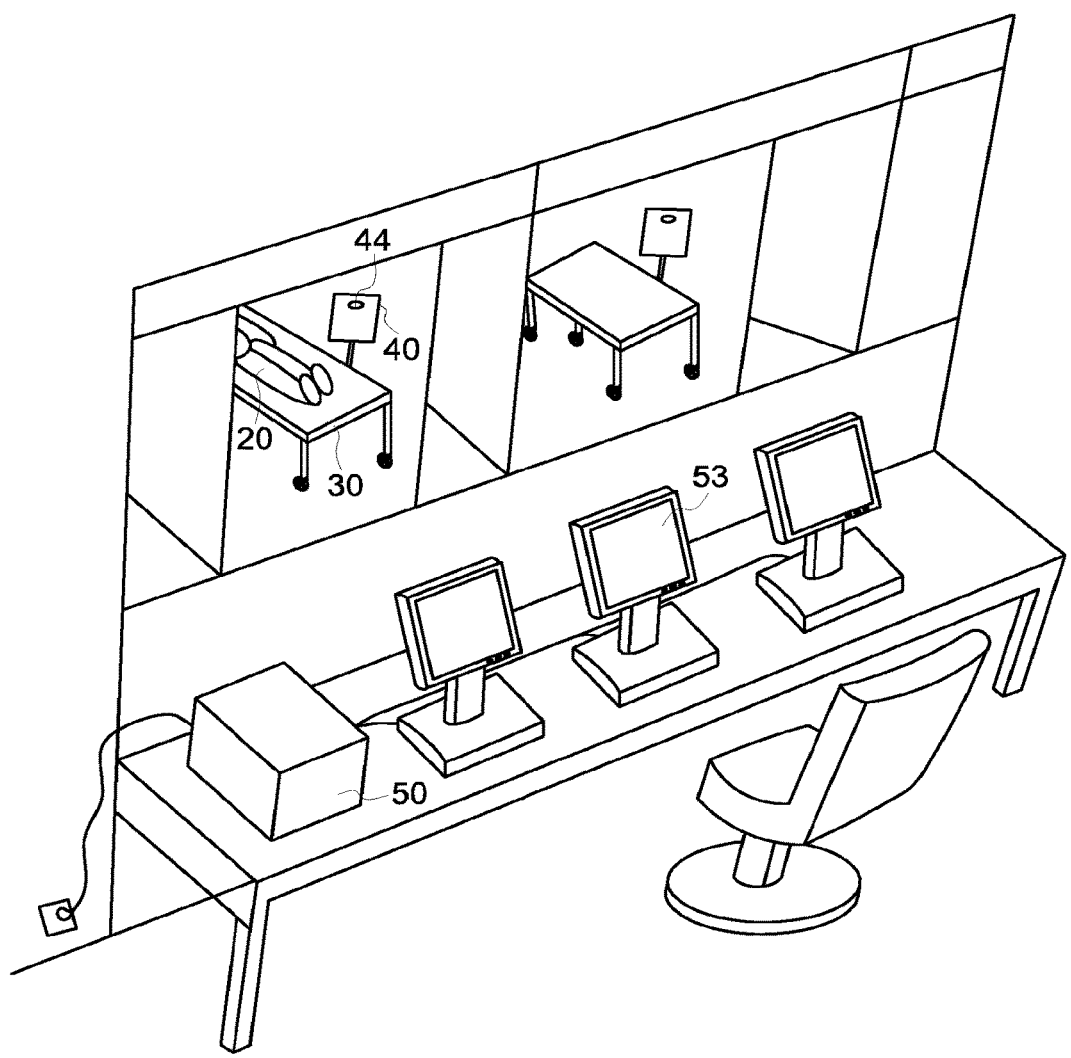
FIG. 3 shows the use of a data reception device comprising a data hub adapted to forward retrieved patient physiological data to a data network.

According to FIG. 3, a wireless patient monitoring device 1, which is connected to a patient 20, is adapted to communicate with a data hub 40, which is positioned at the bedside of a bed 30 upon which a patient 20 is positioned. According to FIG. 3, the wireless patient monitoring device 1 communicates with the data hub 40 using an adapted communication protocol. The communication between the wireless patient monitoring device 1 and the data hub 40 may comprise short range radio communications, such as Bluetooth. The data hub 40 is adapted to forward the data retrieved from the wireless patient monitoring device 1 to a data network, for example comprising a terminal 50. The terminal 50 could be directly provided with a receiver for receiving data emitted by the data hub 40 or could be connected to a receiver via wiring, wherein the receiver is able to communicate with the data hub 40.

A terminal 50 is connected to a screen 53, which is used to allow visual access to retrieved patient physiological data after processing thereof. In the example of FIG. 3, the data hub 40 comprises an identity input device 44 which is adapted to obtain a known patient monitoring device identity to store said patient monitoring device identity in a memory of the data hub 40. To allow the known patient monitoring device identity to be obtained, the wireless patient monitoring device 1 comprises a visual identification, such as the visual identification 11 shown on the wireless patient monitoring device 1 according to FIG. 2. The presence of the visual identification 11 on the exterior of the wireless patient monitoring device 1 and the identity input device 44 allows for a user-friendly and safe procedure for entering the known patient monitoring device identity into the memory of the data hub 40. Once the known patient monitoring device identity has been entered into the memory of the data hub 40, the wireless patient monitoring device 1 can begin retrieving patient physiological data and can commence emitting such retrieved patient physiological data and identification data relating to the identity of the wireless patient monitoring device 1.

The data hub 40 is adapted to receive the identification data and to process said data to obtain an identity for the wireless patient monitoring device which has emitted said identification data. Given that the data hub 40 has stored the known patient monitoring device identity, the data hub 40 is able to compare the known patient monitoring device identity with the identity obtained using the identification data. If the data hub 40 is able to match the known patient monitoring device identity with the obtained identity for the wireless patient monitoring device, the data hub 40 and the wireless patient monitoring device 1 can be paired to allow the data hub 40 to retrieve and process the retrieved patient physiological data. The processing of such data can comprise the forwarding of the data from the data hub to the terminal 50. As shown in the example according to FIG. 3, the embodiment of FIG. 3 allows central reception and analysis of patient physiological data in a central station. The central station allows medical staff to supervise the reception and analysis of patient physiological data of multiple patients in one central location.

The use of the data hub 40 is practical, for example, when a patient 20 is moved from a first location to a second location, wherein the pairing is obtained between the wireless patient monitoring device 1 attached to the patient 20 and a data hub 40 in the presence of which a patient is positioned. The data hub 40 is able to allow pairing in a user-friendly and safe manner. After the pairing has been established, the retrieved patient physiological data can be forwarded to a network comprising a terminal 50 to allow for processing and analysis of the retrieved patient physiological data.

Figure 4:
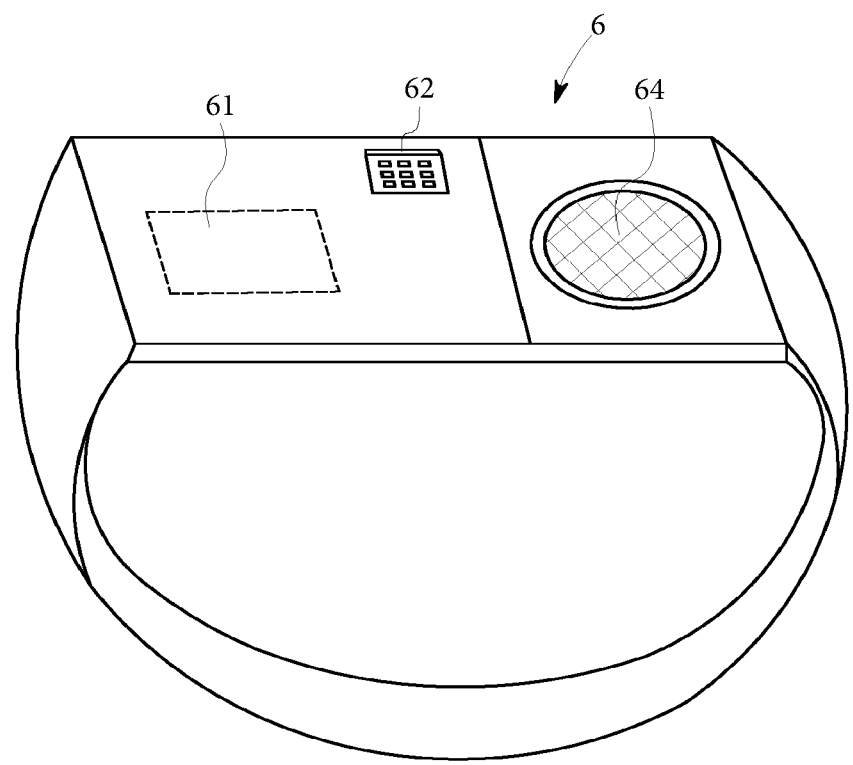
FIG. 4 shows a wireless patient monitoring device according to another exemplary embodiment of the disclosure.

In FIG. 4, an exemplary embodiment of a further wireless patient monitoring device 6 is shown. The wireless patient monitoring device 6 comprises wiring, schematically indicated with the line 62. The wiring relates to an electronic circuit adapted to allow the retrieval of patient physiological data and to allow forwarding of said retrieved patient physiological data in combination with identification data to a data reception device. Moreover, the wireless patient monitoring device 6 comprises a visual identification 61 which allows the visual identification 61 to be read by an optical sensor.

The use of the wireless patient monitoring device 6 is comparable to the use of the wireless patient monitoring device 1 as described with reference to FIGS. 1, 2 and 3. The wireless patient monitoring device 6 according to FIG. 4 comprises an optical sensor 64. The optical sensor 64 may take the form of a camera. The optical sensor 64 is specifically adapted to retrieve patient identity data. The optical sensor 64 is suitable for retrieving biometric patient information. The optical sensor 64 is, for instance, adapted to obtain an image of the fingerprints, retina, blood vessels, thermal picture or other visually readable biomarkers of a patient 20. Additionally or alternatively, the optical sensor 64 is adapted to obtain an image of a barcode or other type of tag attached to a patient. The optical sensor 64 is connected to the wiring 62 to allow data retrieved using the optical sensor 64 to be forwarded to a data reception device.

The actual processing of the images obtained with the optical sensor 64 can be done with the data reception device. This allows the wireless patient monitoring device 6 to have as few electronic components as possible.

The advantage of the wireless patient monitoring device 6, in addition to the advantages described with reference to the wireless patient monitoring device 1, is that it can be used to obtain and forward patient identity data. Thus, the wireless patient monitoring device 6 allows for a safe and user-friendly procedure for entering a patient identity into the memory of a data reception device. For example, where the wireless patient monitoring device 6 is used in combination with the data reception device 2 according to FIG. 1, the patient identity data can be forwarded to the data reception device 2 to be processed and entered into the memory of the data reception device as the known patient identity. Accordingly, the wireless patient monitoring device 6 can be directly paired to the patient with no risk of operator-related errors or the entry of an incorrect identity for the patient.

In practice, a patient file available in the hospital network can be retrieved by scanning a visual identification, such as a QR code, a barcode, or a similar identification, with the effect that patient-related information becomes available on a screen of, for instance, a bedside monitor. Use of the optical sensor 64 allows identification of the patient to which the wireless patient monitoring device 6 is connected to allow establishment of a direct link between the physiological data retrieved using the wireless patient monitoring device 6 and the patient file available on the hospital network. Thus, patient identification is used a reference in the hospital network infrastructure. In this case, the wireless monitoring device 6 publishes the retrieved physiological data to the hospital infrastructure with the patient identification number, such as a social security number, while any monitor connected to the same network can be a subscriber to that particular data. The hospital infrastructure then ensures that all information published in respect of a specific patient identification number is transmitted to those monitors that have subscribed to patient data having the same patient identity number.

According to the invention, it is possible to provide the wireless patient monitoring device with a display. The display could be used to allow direct access to physiological data retrieved by means of the wireless patient monitoring device. The display could also be used for displaying the visual identification, required for pairing the wireless patient monitoring device with a data reception device. The advantage of using a display is that the specific identification visible on the display can be changed, amended or otherwise altered according to the specific use of the wireless patient monitoring device.

What is claimed is:

1. A system for monitoring patient physiological data, comprising:
   a wireless patient monitoring device with a first sensor adapted for retrieving patient physiological data, the wireless patient monitoring device having a known patient monitoring device identity; and
   a data reception device comprising a processor for processing data received from the wireless patient monitoring device and a memory for storing a verification patient monitoring device identity, the memory being connected to an identity input device for entering the verification patient monitoring device identity;
   wherein the wireless patient monitoring device is adapted to send the patient physiological data received and the known patient monitoring device identity to the data reception device using a wireless communication protocol;
   wherein the data reception device is adapted to receive the known patient monitoring device identity, to compare the known patient monitoring device identity to the verification patient monitoring device identity, and to receive and process the patient physiological data when the known patient monitoring device identity matches the verification patient monitoring identity; and
   wherein the wireless patient monitoring device comprises a visual identification corresponding to the known patient monitoring device identity, and wherein the identity input device comprises an optical sensor for retrieving the visual identification.

2. The system according to claim 1, wherein the data reception device comprises a patient monitor with a screen to visualize the patient physiological data, the patient monitor comprising the identity input device.

3. The system according to claim 1, wherein the data reception device comprises a data hub for communicating with the wireless patient monitoring device and adapted to forward the retrieved patient physiological data to a data network, the data hub comprising the identity input device.

4. The system according to claim 3, wherein the data network comprises at least one patient monitor or central station with a screen for visualizing the patient physiological data.

5. The system according to claim 1, wherein the data reception device has a memory for storing an entered patient identity, wherein the wireless patient monitoring device comprises a second sensor for retrieving patient biometric information, wherein the wireless patient monitoring device is further adapted to send the patient biometric information to the data reception device, wherein the processor is further adapted to process the patient biometric information to obtain a received patient identity, to compare the received patient identity with the entered patient identity, and to combine the patient physiological data with the entered patient identity when the received patient identity matches the entered patient identity.

6. The system according to claim 5, wherein the second sensor comprises an optical sensor.

7. The system according to claim 1, wherein the optical sensor comprises a camera.

8. A method for monitoring patient physiological data with a wireless patient monitoring device having a first sensor adapted to retrieve patient physiological data and with a data reception device adapted to receive and process the patient physiological data, the data reception device being connected to a memory, the wireless patient monitoring device having a known patient monitoring device identity, and the wireless patient monitoring device and the data reception device being adapted to communicate using a wireless communication protocol, the method comprising:
   storing a verification patient monitoring device identity in the memory connected to the data reception device;
   sending with the wireless patient monitoring device the known patient monitoring device identity to the data reception device using the wireless communication protocol;
   receiving with the data reception device the known patient monitoring device identity;
   comparing the known patient monitoring device identity to the verification patient monitoring device identity;
   pairing the wireless patient monitoring device with the data reception device to allow the wireless patient monitoring device to retrieve and send the patient physiological data to the data reception device and to allow the data reception device to receive and process the retrieved patient physiological data when the known patient monitoring device identity matches the verification patient monitoring device identity;
   providing the wireless patient monitoring device with a visual identification relating to the known patient monitoring device identity; and
   providing the data reception device with an optical sensor adapted to obtain an image of the visual identification of the wireless patient monitoring device;
   wherein storing the verification patient monitoring device identity in the memory connected to the data reception device includes obtaining an image of the visual identification of the wireless patient monitoring device using the optical sensor of the data reception device and processing the image to retrieve the verification patient monitoring device identity.

9. The method according to claim 8, further comprising providing the data reception device with a screen and visualizing the patient physiological data on the screen.

10. The method according to claim 8, further comprising providing the data reception device with a data hub for communicating with the wireless patient monitoring device and for forwarding the patient physiological data to a data network, providing the data hub with a memory to store the verification patient monitoring device identity, providing the data hub with an optical sensor adapted to obtain an image of the visual identification of the wireless patient monitoring device to allow the data hub to retrieve and store the known patient monitoring device identity, using the wireless patient monitoring device to send sensor identification data to the data hub, using the data hub to receive and process the sensor identification data to retrieve the known patient monitoring device identity of the wireless patient monitoring device, comparing the known patient monitoring device identity retrieved using the data hub with the verification patient monitoring device identity stored in the memory, and pairing the wireless patient monitoring device with the data hub to allow the wireless patient monitoring device to retrieve and send the patient physiological data and to receive and process the patient physiological data with the data hub when the known patient monitoring device identity matches the verification patient monitoring device identity.

11. The method according to claim 8, further comprising providing the wireless patient monitoring device with a second sensor for retrieving biometric patient information, using the wireless patient monitoring device to send the biometric patient information to the data reception device, and using the data reception device to process the biometric patient information to obtain a received patient identity.

12. The method according to claim 11, further comprising using the memory of the data reception device to store an entered patient identity, using the data reception device to compare the entered patient identity with the received patient identity, and combining the patient physiological data with the entered patient identity when the received patient identity matches the entered patient identity.

* * * * *